(12) United States Patent
Meerbeek et al.

(10) Patent No.: US 10,080,633 B2
(45) Date of Patent: Sep. 25, 2018

(54) TOOTHBRUSH WITH VARIABLE TOUCH SELECTION SYSTEM AND METHOD OF OPERATION THEREOF

(71) Applicant: KONINKLIJKE PHILIPS N.V., Eindhoven (NL)

(72) Inventors: Berent Willem Meerbeek, Eindhoven (NL); Jonathan David Mason, Waalre (NL); Dzmitry Viktorovich Aliakseyeu, Eindhoven (NL); Sanae Chraibi, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 284 days.

(21) Appl. No.: 15/102,359

(22) PCT Filed: Nov. 3, 2014

(86) PCT No.: PCT/IB2014/065758
§ 371 (c)(1),
(2) Date: Jun. 7, 2016

(87) PCT Pub. No.: WO2015/087176
PCT Pub. Date: Jun. 18, 2015

(65) Prior Publication Data
US 2016/0317267 A1    Nov. 3, 2016

Related U.S. Application Data

(60) Provisional application No. 61/915,207, filed on Dec. 12, 2013.

(51) Int. Cl.
*B08B 3/00* (2006.01)
*A61C 17/22* (2006.01)
(Continued)

(52) U.S. Cl.
CPC .............. *A61C 17/222* (2013.01); *A46B 9/04* (2013.01); *A46B 9/10* (2013.01); *A46B 15/0004* (2013.01);
(Continued)

(58) Field of Classification Search
None
See application file for complete search history.

(56) References Cited

U.S. PATENT DOCUMENTS 3,463,990 A    8/1969    Ross
4,243,388 A    1/1981    Arai
(Continued)

FOREIGN PATENT DOCUMENTS

CN    1091621 A    9/1994
CN    2593632    12/2003
(Continued)

*Primary Examiner* — Eric W Golightly

(57) ABSTRACT

An oral cavity apparatus includes a body portion having first and second ends and a grip portion; an oral tool coupled to the first end of the body portion; and a touch-sensitive (TS) sensor which is located on the body portion and outputs a sensor value indicative of a force applied thereto by a user. In addition, a controller is configured to compare the sensor value with at least one threshold value, and to actuate the oral tool based upon the results of the comparison.

15 Claims, 12 Drawing Sheets

(51) Int. Cl.
*A46B 15/00* (2006.01)
*A61C 17/02* (2006.01)
*A61C 1/00* (2006.01)
*H03K 17/96* (2006.01)
*A46B 9/04* (2006.01)
*A46B 9/10* (2006.01)
*A61C 17/34* (2006.01)

(52) U.S. Cl.
CPC ........ *A46B 15/0012* (2013.01); *A61C 1/0015* (2013.01); *A61C 17/02* (2013.01); *A61C 17/221* (2013.01); *A61C 17/3481* (2013.01); *H03K 17/9625* (2013.01); *A61C 17/227* (2013.01); *H03K 17/962* (2013.01); *H03K 17/964* (2013.01); *H03K 2017/9602* (2013.01)

(56) References Cited

U.S. PATENT DOCUMENTS

| | | | |
|---|---|---|---|
| 4,409,701 A | 10/1983 | Perches | |
| 5,350,248 A | 9/1994 | Chen | |
| 5,493,747 A | 2/1996 | Inakagata et al. | |
| 6,037,724 A | 3/2000 | Buss et al. | |
| 6,161,245 A | 12/2000 | Weihrauch | |
| 8,214,958 B2 | 7/2012 | Pinyayev et al. | |
| 8,239,995 B2 | 8/2012 | Chenvainu et al. | |
| 8,497,836 B2 | 7/2013 | Toebes et al. | |
| 2008/0002035 A1 | 1/2008 | Yoshida | |
| 2011/0247155 A1 | 10/2011 | Hilscher et al. | |
| 2012/0203213 A1 | 8/2012 | Kimball et al. | |

FOREIGN PATENT DOCUMENTS

| | | | | |
|---|---|---|---|---|
| CN | 1893889 A | 1/2007 | | |
| CN | 101193605 A | 6/2008 | | |
| CN | 101490642 A | 7/2009 | | |
| CN | 101511222 A | 8/2009 | | |
| CN | 101668493 | 3/2010 | | |
| CN | 102016870 | 4/2011 | | |
| CN | 103315779 | 9/2013 | | |
| DE | 19500107 A1 * | 7/1996 | ............... | A46B 7/02 |
| DE | 202005004368 U1 | 4/2005 | | |
| EP | 2641550 A2 | 9/2013 | | |
| GB | 2478722 A | 9/2011 | | |
| JP | 06169814 A * | 6/1994 | | |
| JP | 2009219757 | 10/2009 | | |
| JP | 20130346636 A | 2/2013 | | |
| WO | 2008147360 A1 | 12/2008 | | |
| WO | 2012042493 A1 | 4/2012 | | |

* cited by examiner

TOOTHBRUSH WITH VARIABLE TOUCH SELECTION SYSTEM AND METHOD OF OPERATION THEREOF

CROSS-REFERENCE TO PRIOR APPLICATIONS

This application is the U.S. National Phase application under 35 U.S.C. § 371 of International Application No. PCT/IB2014/065758, filed on Nov. 3, 2014 which claims the benefit of U.S. Provisional Patent Application No. 61/915,207, filed on Dec. 12, 2013. These applications are hereby incorporated by reference herein.

The present system relates to a toothbrush system and, more particularly, to an electronic toothbrush system having a touch-sensitive body for selection of one or more functions, and a method of operation thereof.

BACKGROUND OF THE INVENTION

Oral healthcare devices are used for oral healthcare and typically include electronic toothbrushes and water-based inter-dental cleaning devices. Electronic toothbrushes typically have rotating and/or vibrating heads with bristles which contact the teeth of a user so as to clean teeth and/or remove plaque. A well-known vibrating-type toothbrush is known as the Philips Sonicare™ toothbrush and has a vibrating head. Water-based inter-dental cleaning devices, such as the Philips Airfloss™ and the like, typically use water as a cleaning medium and have a head which ejects a directed water jet to forcibly remove debris from between teeth of a user. To activate most oral-healthcare devices (e.g., electronic toothbrushes and water-based inter-dental cleaning devices), a user must depress a small on/off button. This button is prone to collect debris, and is difficult to find during use, especially when a user is not looking directly at the oral healthcare device.

BRIEF SUMMARY OF THE INVENTION

The system(s), device(s), method(s), arrangements(s), user interface(s), computer program(s), processes, etc. (hereinafter each of which will be referred to as system, unless the context indicates otherwise), described herein address problems in prior art systems.

In accordance with embodiments of the present system, there is disclosed an oral cavity apparatus comprising a body portion having first and second ends and a grip portion; an oral tool coupled to the first end of the body portion; a touch-sensitive (TS) sensor which is located on the body portion and outputs a sensor value indicative of a force applied thereto by a user; and a controller configured to compare the sensor value with at least one threshold value, and to actuate the oral tool based upon the results of the comparison.

The oral tool may comprise at least one of a toothbrush, a water nozzle, an airfloss and a drill, and the TS sensor may comprise a force-sensitive resistor which outputs a value of resistance, and may include a plurality of polymer layers which are laminated upon each other and which substantially encircle the body portion. The sensor value may be a resistive value which is proportional to the force applied to the TS sensor.

In addition, the controller may be further configured to determine a frequency to reciprocally drive the oral tool in accordance with results of the comparison. The controller may be further configured to determine the frequency to drive the oral tool in accordance with the sensor value based upon a one-to-one basis, and/or upon a discrete basis. To actuate the oral tool, the controller may control an actuator which is coupled to the oral tool to provide an electromotive force to the oral tool, where the actuator comprises at least one of a rotary motor, a linear motor, and a pump. A fluid reservoir may be coupled to the pump.

Another embodiment includes a method of actuating an oral cavity apparatus having a body portion and an oral tool extending from the body portion, the oral tool coupled to an actuator, the body portion having a grip portion situated between opposed ends of the body portion, the method performed by at least one controller of the oral cavity apparatus and comprising acts of: obtaining sensor information generated by a touch-sensitive (TS) sensor situated at the grip portion of the body portion, the sensor information corresponding to a force applied by a user to a surface of the TS sensor; selecting a function from a plurality of functions based upon the sensor information; and controlling the actuator in accordance with the selected function. The method may further comprise an act of forming, by the TS sensor, the sensor information to comprise an impedance value, e.g., resistive and/or capacitive value, corresponding to the force applied by the user to the surface of the TS sensor. The TS sensor may comprise at least one ring which encircles the body portion. The act of selecting a function from a plurality of functions may comprises an act of determining a frequency at which to drive the actuator in accordance with the sensor information on a one-to-one and/or a discrete basis. The method may further comprise an act of controlling a further actuator to control and extension of bristles from the oral tool in accordance with the selected function.

Yet another embodiment includes a non-transitory computer readable medium comprising computer instructions which, when executed by a processor or controller, configure the processor/controller to control operation of the oral cavity apparatus by performing the acts of the above described method.

The present invention is explained in further detail in the following exemplary embodiments and with reference to the figures, where identical or similar elements are partly indicated by the same reference numerals, and the features of various exemplary embodiments being combinable. In the drawings:

DETAILED DESCRIPTION OF THE INVENTION

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements.

Figure 1:
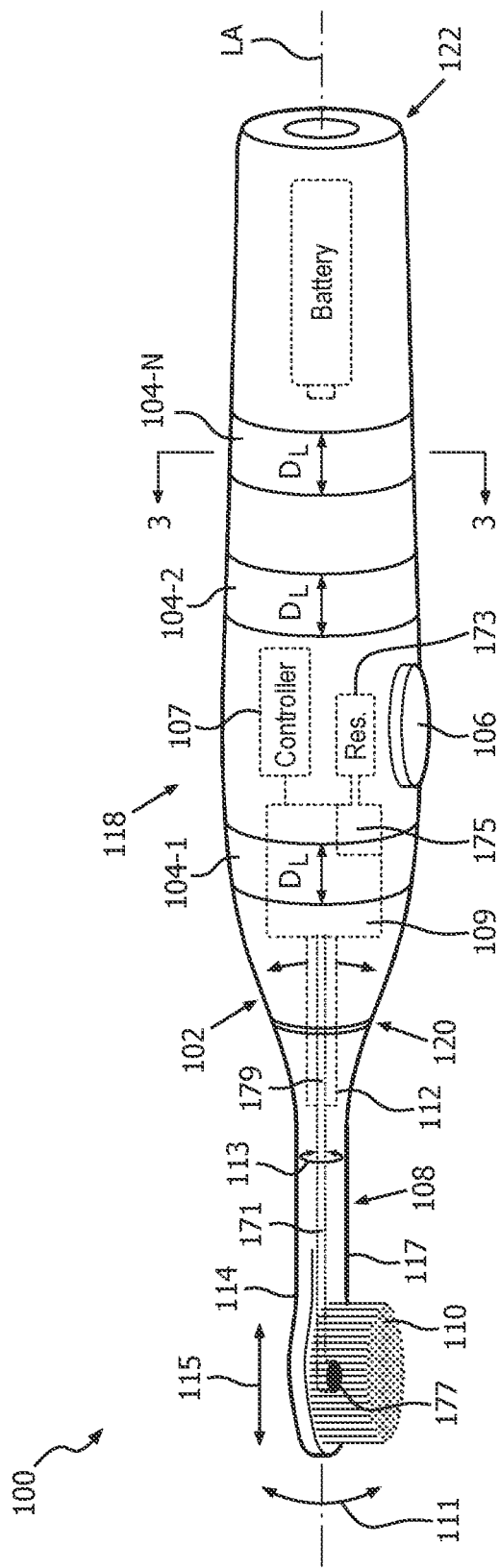
FIG. 1 shows a front perspective view of a portion of toothbrush system with a touch-sensitive body in accordance with embodiments of the present system.

FIG. 1 shows a front perspective view of a portion of toothbrush system 100 (hereinafter system 100 for the sake of clarity) with a touch-sensitive body portion 102 (also referred to as a body 102) in accordance with embodiments of the present system. The touch-sensitive (TS) body 102 may have first and second ends 120 and 122, respectively, a grip portion 118 (also referred to as hand grip 118) situated between the first and second ends 120 and 122, respectively, and one or more touch-sensitive (TS) sensors such as touch-sensitive (TS) rings 104-1 through 104-N (generally 104-$x$) and/or a button-type TS sensor 106 (shown as a circular button) configured in any suitable arrangement. The TS rings 104-$x$ may extend along a longitudinal axis (LA) of the body 102 by a distance $D_L$ and which may substantially encircle the body 102. The various TS rings 104-$x$ may have the same or different distances $D_L$. The TS sensors (e.g., including 104-$x$ and/or 106) may sense a force exerted thereupon (e.g., by a user) and form corresponding sensor information. This sensor information may then be provided to a controller or processor 107 of the system 100 for further processing. While the TS sensors 104-$x$ and/or 106 are shown as rings, it should be understood that any desired shaped TS sensors may be used, where the number and distribution of TS sensors or sensor points/areas may be chosen to discriminate different squeeze actions and/or to avoid false actions or errors.

The TS sensors (e.g., 104-$x$ and/or 106) may sense a force that a user applies to portions of the hand grip 118 which have TS sensors (104-$x$ and/or 106) using any suitable sensory method. For example, the TS sensors may include force-sensitive (FS) sensors such as strain-gauge, piezoelectric, capacitive, and/or resistance type sensors which may be integrated in the hand grip 118 of the body 102. The FS resistance-type sensors may include one or more force-sensing resistors having a conductive polymer, which may change resistance in a predictable manner following application of a force to one or more parts of its surface. This resistance may then be output as sensor information for further processing by the controller 107. More particularly, the controller 107 may translate the output resistance into a value indicating a force applied by the user upon the corresponding FS sensor. As the force applied by the user increases, the resistance increases and the value indicating the force applied by the user upon the corresponding FS sensor may increase correspondingly (e.g., linearly, etc.). It is also envisioned that embodiments of the present system may include a plurality of TS sensors (e.g., arranged as an array, a matrix, etc., in certain areas, in a desired configuration, etc.) to improve the detection of squeeze actions and/or to provide information indicative of an area of the handgrip 118 to which a force is being applied.

An oral cleaning tool 108 (also referred to as a tool 108) configured for oral cleaning may be coupled to the body 102 using any suitable method (e.g., a friction fit, etc.). The tool 108 may include a tool body 117 and may include a toothbrush head 114 (also referred to as a brushhead or toothbrush 114) having brushes 110 (bristle, rubber, etc.). In addition or alternately, the tool body 117 and may include may include a water nozzle. The tool 108 may be coupled to an actuator 109, such as an electromotive driver, using any suitable method such as via an actuator rod 112 so as to be driven by the electromotive driver. However, in yet other embodiments, the tool 108 may be coupled to the actuator 109 using a magnetic coupling. The electromotive driver may include rotational, linear, or vibrating motors which may output corresponding motion and/or a transmission which may convert motion to a desired type (e.g., rotational motion to oscillating rotational motion, etc.). For example, a motor is used that is configured to produce vibrations in a broad frequency range as to create meaningful and noticeably different operational modes for end-users, e.g., a sonic (9000 to 40000 movements per minute) or ultrasonic motor (>2400 movements per minute).

In the present embodiments, it will be assumed that the actuator 109 may output an oscillating motion as shown by arrow 111 to drive the tool 108. In yet other embodiments, the tool 108 may receive a reciprocating rotational motion as shown by arrows 115, 113. In yet other embodiments, the tool 108 may include a transmission which may convert direction of an output of the electromotive driver 109. In yet other embodiments, it is envisioned that the brushhead 114 may be coupled to one or more carriers which may be coupled to the electromotive driver 109 (e.g., directly or via any suitable linkage and/or transmission system) and may move relative to the cleaning tool body 117.

It is further envisioned that in some embodiments, a fluid flow path 179 may be fluidly coupled between a fluid reservoir 173 and an opening 177 of the tool 108. An fluid actuator 175 (e.g., a fluid pump) may be operative, under the control the controller 107, to control flow of the fluid from the reservoir 173 along the fluid flow path 179 to be ejected at the opening 177. Accordingly, the fluid actuator 175 may be operative to pressurize the fluid. The fluid flow path 179 may include a flow passage 171 situated between an end of the actuator rod 112 and the opening 177. The fluid flow path 179 may further include a flow passage in the actuator rod 112 that is fluidly coupled to the fluid actuator 175. The fluid actuator 175 may further be coupled to the fluid reservoir 173 which may include a desired fluid (e.g., water, cleaning fluid, abrasive fluid, toothpaste, etc.) and may pressurize the desired fluid so that it flows from the fluid reservoir 173 through the opening 177 along the fluid flow path 179, under the control of the controller and in accordance with pressure or force applied to the touch-sensitive sensor(s) (104-x and/or 106) on the body 102. In some embodiments, a plurality of fluid reservoir s and tool openings may be provided, where the fluid flow path 179 may include a plurality of fluid flow paths, each provided between a corresponding fluid reservoir and a corresponding opening in the tool. Each of the plurality of fluid flow paths may include a fluid actuator to pressurize a fluid along the corresponding fluid flow path under the control of the controller 107.

Figure 2:
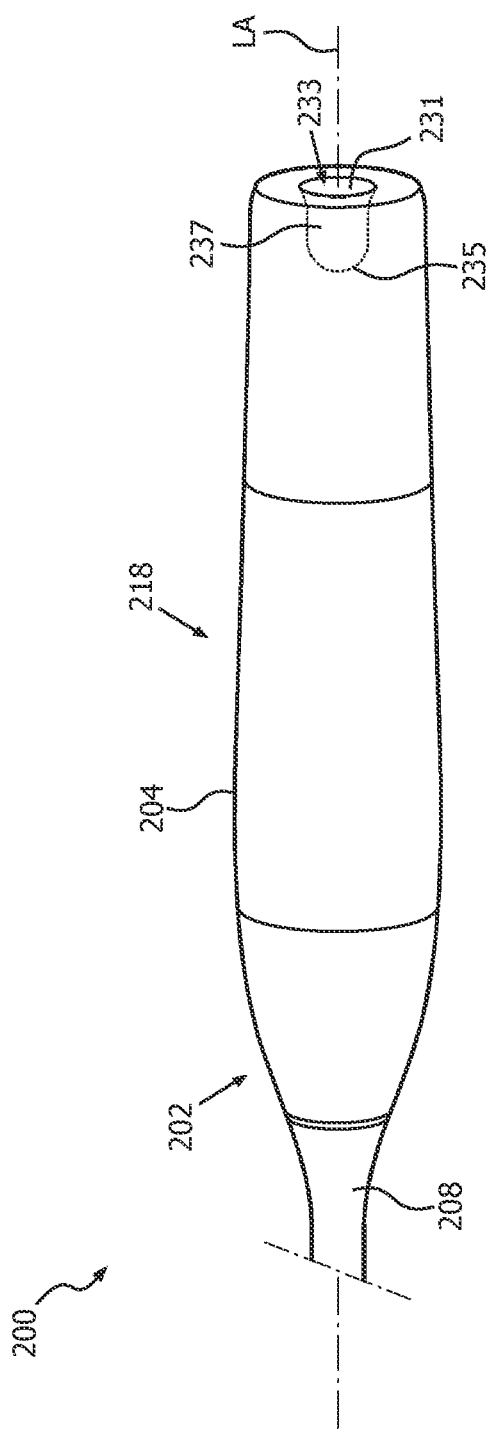
FIG. 2 shows a front perspective view of a portion of a toothbrush system with a touch-sensitive body in accordance with other embodiments of the present system.

FIG. 2 shows a front perspective view of a portion of a toothbrush system 200 with a touch-sensitive body 202 in accordance with other embodiments of the present system. The toothbrush system 200 is similar to the toothbrush system 100 and includes the body 202, a touch-sensitive ring 204, and a tool 208, which are similar to the body 102, the touch-sensitive ring(s) 104-x, and the tool 108, respectively, of the toothbrush system 100. However, the touch-sensitive ring 204 extends along a length of a handle portion 218 of the body 202 such as by a substantial or major length. Accordingly, the touch-sensitive ring 204 may extend along a major length of the longitudinal axis (LA) of the body 202. A charging/retention port 231 may be provided to couple the body 202 to a charging base, if desired. The charging/retention port 231 may include an opening 233 leading to a cavity 237 having a closed end 235 opposite to the opening 233.

Figure 3:
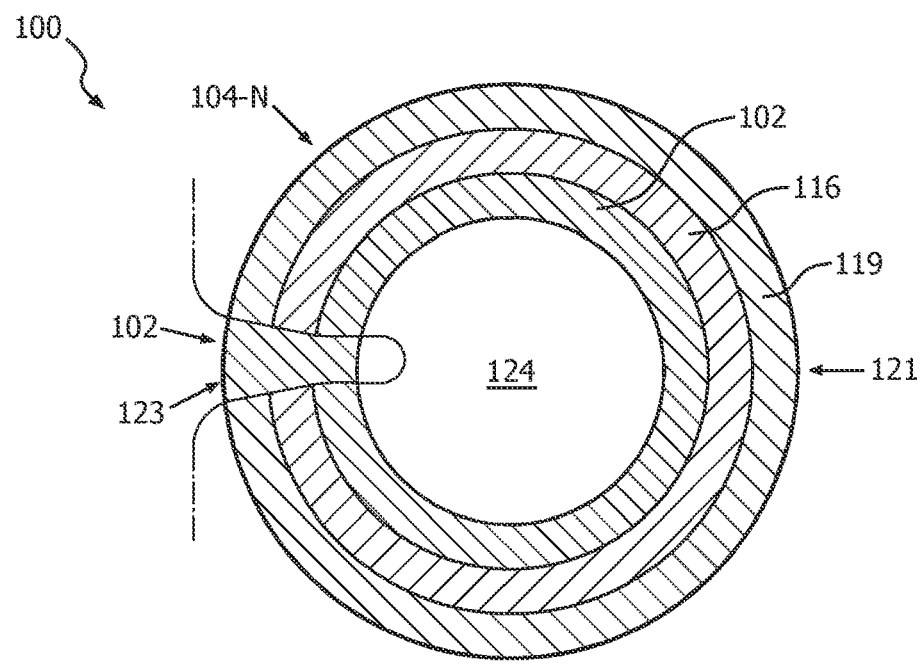
FIG. 3 shows a cross section of a portion of the toothbrush system taken along lines 3-3 of FIG. 1 in accordance with embodiments of the present system.

FIG. 3 shows a cross section of a portion of the toothbrush system 100 taken along lines 3-3 of FIG. 1 in accordance with embodiments of the present system. The TS ring 104-N may include an outer cover 119 and a pressure sensor 116. The TS ring 104-N may encircle (or substantially encircle) the body portion 102. The pressure sensor 116 may include a touch-sensitive pressure sensor which may sense pressure applied thereto and form a corresponding pressure signal which may be provided to the controller 107 (FIG. 1) for further processing. This signal may be an analog or digital signal. However, in embodiments of the present system it will be assumed that this signal is an analog signal indicating resistance as a function (linear, etc.) of pressure applied to the pressure sensor. The pressure sensor 116 may use any suitable touch-sensitive sensor method. For example, the pressure sensor 116 may include impedance sensors, such as resistive and/or capacitive-type touch-sensors, etc. and may be rolled in a circular or semicircular shape so as to sense pressure in a cylindrical area or the like, if desired. An exterior surface of the pressure sensor 116 may be flush with an exterior surface of surrounding portions of the body 102. For example, the TS ring 104-N (and/or the other TN rings 104-x) may have an outer surface 121 which may be flush or substantially flush with an exterior surface 123 of the body portion 102. This outer surface 121 may further be sealed to surrounding exterior portions of the body 102 so to seal the sensor from contamination, such as water and/or debris. The body 102 may include a cavity 124 configured to receive at least a portion of one or more of a charger (e.g., an inductive charger), the controller 107, the actuator 109, and the actuator rod 112 shown in FIG. 1. The body 102 may include notches or cutout areas along a surface thereof to receive one or more of the TS sensors (106, 114-x, etc.), if desired.

In some embodiments, the pressure sensor 116 may include a plurality of pressure zones (e.g., a pressure zone matrix), each of which may detect pressure applied thereto. Accordingly, the pressure sensor 116 may form a signal indicative of the pressure zone(s) to which pressure is being applied and, for example, the controller 107 may then recognize these pressure patterns using any suitable method. Then, the recognized patterns may then be used to identify a user or type of user (e.g., large hand=adult, small hand=child) and configure operation (e.g., by controlling the actuator 109) of the toothbrush system 100 in accordance with the recognized user or type of user, etc.

In some embodiments, it is envisioned that the pressure sensor 116 may include capacitive sensors which may detect the presence of a user's hand (e.g., with or without touch) and form a corresponding signal based upon a distance between a user's hand and an adjacent portion of the pressure sensor and/or a force applied to the pressure sensor. It is further envisioned that pressure sensor 116 may include touch-screen-type sensors and/or may include a pressure matrix which may determine a position of pressure applied thereto and/or a position of a users hand in the vicinity of the sensor, if desired, and provide this information to the controller 107 for further processing.

In yet other embodiments, the toothbrush 102 may be configured such that one or more of the TS sensors (e.g., 104-x and/or 106) may be configured to function as an on/off switch as well as touch-sensitive switch (e.g., a pressure-sensitive switch). For example, once the toothbrush is turned (e.g., the actuator 109 is driven by the controller 107) on as a result of a user applying force to one or more selected TS sensors (e.g., 104-x and/or 106), the controller 107 may determine a value of a force applied (e.g., an analog resistive value) to the corresponding TS sensor (e.g., 104-x and/or 106). Then, based upon the value of the force applied, the controller 107 may determine a function to apply and activate the actuator 109 in accordance with the determined function. Thus, a user may hold the hand grip 118, turn the toothbrush on by depressing the TS sensor 106 once and, thereafter, press and hold the TS sensor 106 using a desired pressure and/or pattern. Then, the controller 107 may read force values from the TS sensor 106 (which are related to a force applied thereto) and select a desired function to activate. The functions may include functions such as massage function, a deep clean function, a light clean function, a beginner's function, a training function, a child user function, an adult user function, etc. Each of these functions may have a predefined defined frequency, pattern, amplitude, etc. The controller 107 may then control the actuator 109 to operate in accordance with the selected function. In yet further embodiments, one or more of the TS sensors (e.g., 104-x, 106) may be ergonomically positioned on the body 102 and/or may be ergonomically shaped so as to enhance ease of user and/or user comfort when holding and/or operating the toothbrush system 100.

Figure 4:
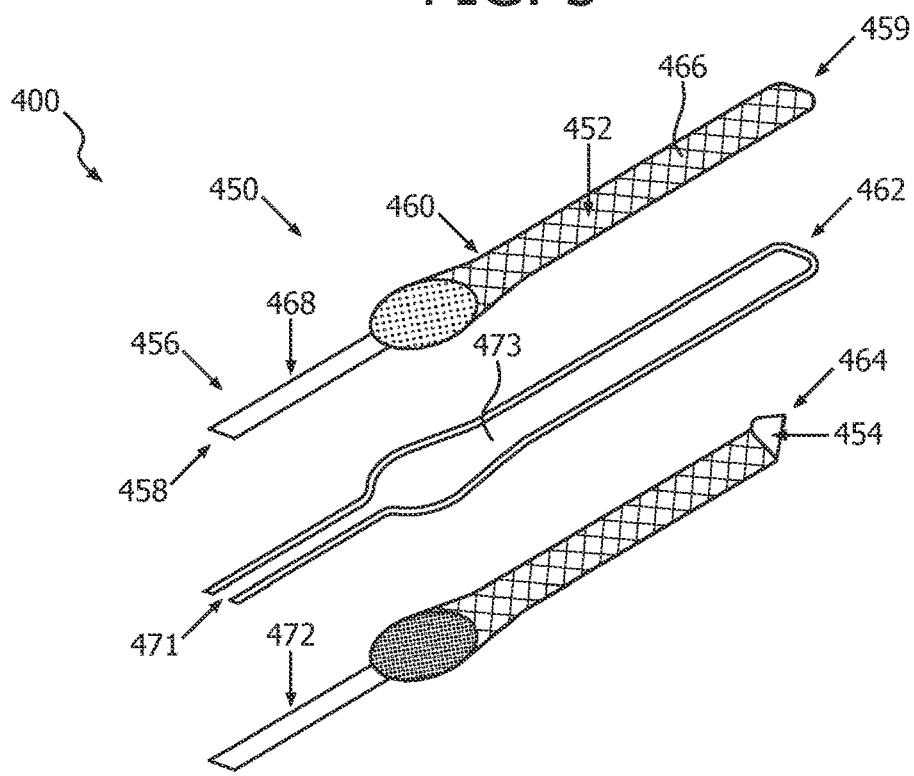
FIG. 4 shows an exploded perspective view of a force-sensitive resistor type pressure sensor in accordance with embodiments of the present system.

FIG. 4 shows an exploded perspective view of a force-sensitive (FS) resistor type pressure sensor 400 in accordance with embodiments of the present system. The pressure sensor 400 may include a conductive polymer laminate 450 having first and second major surfaces 452 and 454, respectively, first and second ends 458 and 459, respectively, and may change resistance in a predictable manner (e.g., linearly, etc.) following application of a force to one or more of its surfaces such as the first and second major surfaces 452 and 454, respectively. This resistance may be translated into a force value (e.g., an analog value or digital value, if desired) indicating a magnitude of the force applied to the pressure sensor 400 and may be output at an output lead assembly 456 of the pressure sensor 400. Accordingly, as the force increases, the force value may increase correspondingly (e.g., linearly, etc.). An analog-to-digital convert (A/D) may be provided to convert the force value from analog to digital form, if desired. The pressure sensor 400 may include a plurality of polymer layers such as an active layer 460 defining an active area, a spacer layer 462, such as a non-conductive plastic layer, and a conductive film layer 464 formed over a flexible substrate 465, shown in FIG. 6. The active layer 460 may include a conductive layer 466 and an electrical lead 468 coupled thereto. The spacer layer 462 may include an opening or air vent 471 to a cavity 473 which may be operative to equalize pressure between the active layer 460 and the conductive film layer 464. The conductive film layer 464 may include an electrical lead 472 coupled thereto. The resistive value may be read across the electrical leads 468 and 472 which may be configured to be coupled the controller, if desired.

Figure 5:
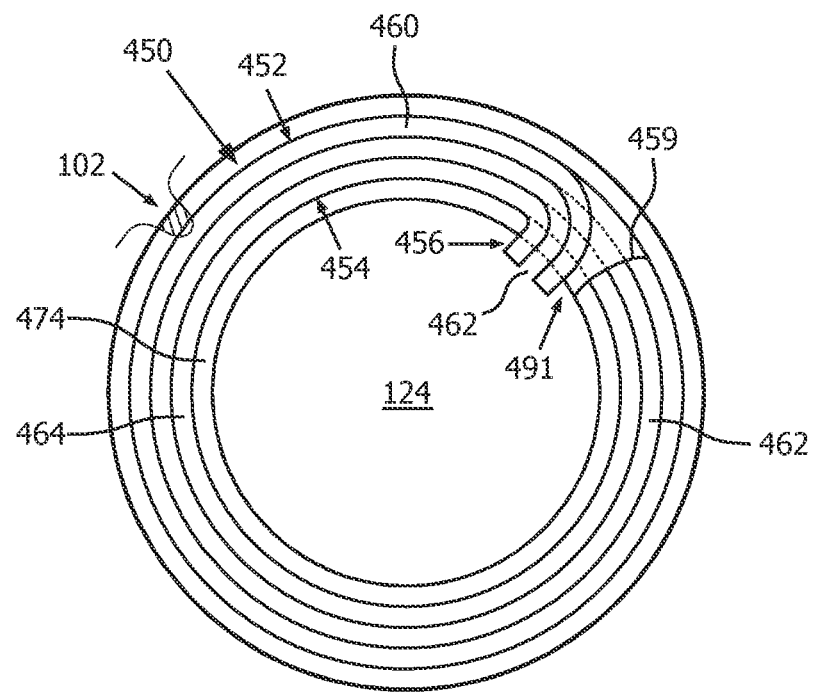
FIG. 5 shows a side-view of a force-sensitive resistor type pressure sensor installed in accordance with embodiments of the present system.
Figure 6:
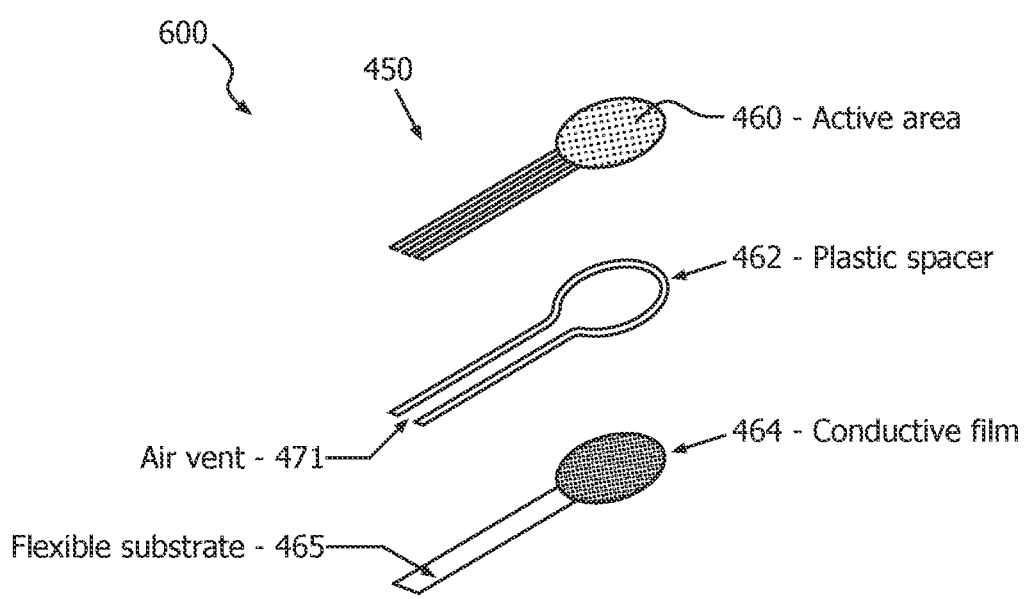
FIG. 6 shows an exploded perspective view of a force-sensing resistor type pressure sensor in accordance with embodiments of the present system.

FIG. 5 shows a side-view of a force-sensitive (FS) resistor type pressure sensor 400 installed in accordance with embodiments of the present system. A support portion 474 may support for the FS resistor pressure sensor 400 (hereinafter pressure sensor 400) and may be formed integrally with the body 102 or may be formed separately from the body 102 and inserted within the cavity 124 of the body 102, if desired. The lead assembly 456 may be folded to pass through one or more openings 491 in the body 102, if desired. However, in yet other embodiments, one or more vias may be provided through the body 102 and/or one or more layers (e.g., 460, 462, 464) of the pressure sensor 400. Accordingly, the lead assembly 456 may be configured to receive the one or more vias. The pressure sensor 400 may have any suitable size and/or shape. For example, in some embodiments, the pressure sensor 400 may form at least part of a ring which may extend fully or substantially about the body 102. However, in yet other embodiments, the pressure sensor may have yet other shapes such as shown in FIG. 6 which shows an exploded perspective view of a force-sensing resistor type pressure sensor 600 (hereinafter pressure sensor 600) in accordance with embodiments of the present system. The pressure sensor 600 may be configured similarly to the pressure sensor 400 of FIG. 4 and similar numerals are shown for the sake of clarity. However, the size and/or shape may be different. For example, the pressure sensor 600 may be used for the button-type TS sensor 106. In yet other embodiments, it is envisioned that the pressure sensor 400 may form an arc shape (when viewed from the side) which may extend about the body 102.

Figure 7:
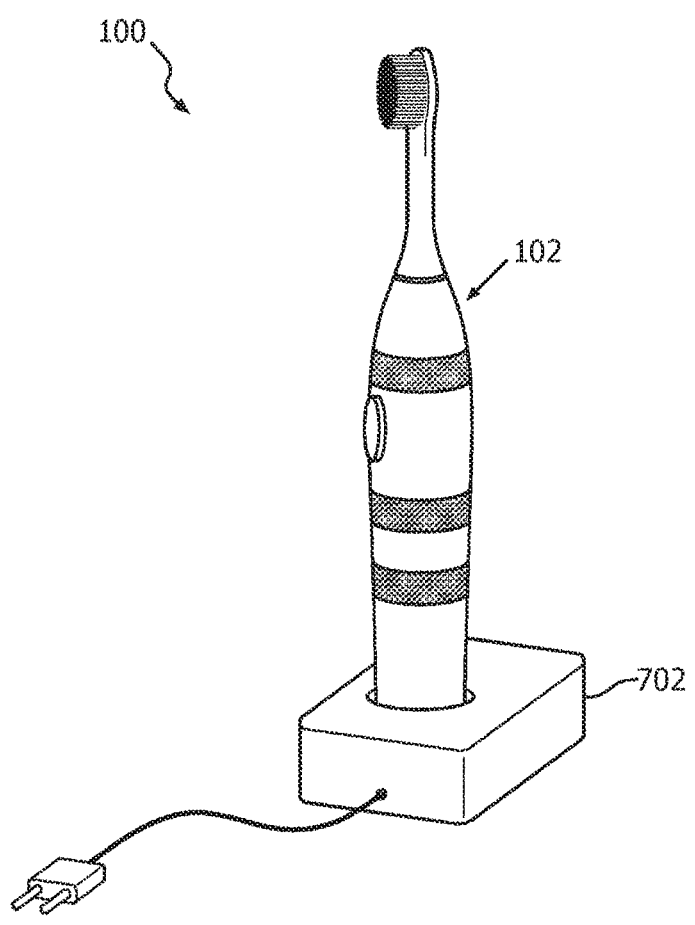
FIG. 7 shows a side perspective view of a portion of toothbrush system situated on a charging stand in accordance with embodiments of the present system.

FIG. 7 shows a side perspective view of a portion of toothbrush system 100 situated on a charging stand 702 in accordance with embodiments of the present system. The body 102 may be a touch-sensitive body and may be configured to be coupled to the charging stand 702 so as to wirelessly receive an electrical power suitable for charging and/or operation therefrom.

A method of operation for oral healthcare devices (OHD) (such as the toothbrush system 100, etc.) operating in accordance with embodiments of the present system will now be discussed. Upon detecting that a user has squeezed a grip portion of the OHD, a controller may determine an amount (e.g., magnitude) of force and/or pattern of force (e.g., pattern of squeezes) and control the OHD to perform one or more functions associated with the determined amount of force and/or pattern of force. The pattern may be detected when different forces are applied over a time interval such as three seconds. However, other time intervals may also be used. Table 1 illustrates a function selection table in accordance with embodiments of the present system.

TABLE 1

Function Selection Table

| Applied Force | | | Cleaning Mode Functions | |
|---|---|---|---|---|
| Detected Force on Handgrip | Pattern | Time | Toothbrush | Flosshead |
| High (e.g., squeeze with great force) Detected Force >= threshold2 | N/A | Less than 3 seconds | Increase operating frequency. For example, by increasing the speed of rotation (RPM) or frequency of vibrations of the brush head accordingly (e.g., proportionally to force) | |
| Low (e.g., the handgrip is loosely held) Detected Force < threshold2 | N/A | Less than 3 seconds | Decrease operating frequency or RPM. For example, by decreasing the speed of rotation or vibrations of the brushing head. | |

TABLE 1-continued

Function Selection Table

| Detected Force on Handgrip | Applied Force | | Cleaning Mode Functions | |
|---|---|---|---|---|
| | Pattern | Time | Toothbrush | Flosshead |
| Low | Squeeze Twice (e.g., squeeze and loosen grip twice (above first threshold) within 2 seconds) | | Change vibration rhythm of brushhead to a more pulsating vibration to remove stuck small elements. (e.g., increase frequency of pulsating cycles at a given frequency such as a threshold frequency). | |
| Light (e.g., Threshold1 >= Detected Force > Threshold2) | Squeeze Action 1 | | Activate integrated cartridge (e.g. containing a desired cleaning agent such as toothpaste, mouthwash, etc.), to release one or more desired cleaning agents through the brush head. The firmer the squeeze, the more cleaning agent will be released. Activation may be performed for predetermined activation time for this function such as 5 seconds, etc. | |
| Medium (e.g., Threshold2 >= Detected Force > Threshold3) | Squeeze Action 2 | | | Activate interdental cleaning device to provide jets with micro-droplets of water to remove dirt in between teeth. Activation may be performed for predetermined activation time for this function such as 5 seconds, etc. |
| Hard (e.g., Threshold3 >= Detected Force) | Squeeze Action 3 | | Activate pump to provide vacuum for removing debris from teeth. Activation may be performed for predetermined activation time for this function such as 5 seconds, etc. | Activate pump to provide vacuum for removing debris from teeth. Activation may be performed for predetermined activation time for this function such as 5 seconds, etc. |
| Hard (e.g., Threshold3 >= Detected Force) | N/A | More than 3 seconds | Activate bristles of the second type. (e.g., extend firm bristles). Apply voltage (e.g., greater than Vthresh) to EAP polymer. Activation may be performed for predetermined activation time for this function such as 5 seconds, etc. | |
| No force detected or detected force <= off threshold force | N/A | More than 2 seconds | Turn Off | Turn Off |
| Treshold1 <= Detected Force < Threshold2 | | More than 2 seconds | Operate at first frequency (e.g., as set by the user and/or system) | |
| Treshold2 <= Detected Force < Threshold3 | | More than 2 seconds | Operate at second frequency (e.g., as set by the user and/or system) | |

TABLE 1-continued

Function Selection Table

| Applied Force | | | Cleaning Mode Functions | |
|---|---|---|---|---|
| Detected Force on Handgrip | Pattern | Time | Toothbrush | Flosshead |
| Treshold3 <= Detected Force < Threshold4 | | More than 2 seconds | Operate at third frequency (e.g., as set by the user and/or system) | |
| Treshold4 <= Detected Force | | More than 2 seconds | Operate at fourth frequency (e.g., as set by the user and/or system) | |

The various squeeze actions, such as squeeze actions 1-3 may include squeezing, maintaining the squeezing force, and releasing and loosening the force/grip on the handgrip 118 (or portions thereof) once, and depending on how hard the user squeezed handgrip 118, the amount of released agent is defined. To distinguish the squeeze actions from other actions, such as grabbing the handgrip 118, or continuously squeezing to change the operating frequency, for example, a desired action such as release of an agent (e.g., toothpaste or cleanser) is only activated and performed if the squeeze and release events happen in a predefined time window or range, such as within between 0.1 to 0.2 seconds. Thus, a squeeze action may be defined as hardening and releasing of the grip that happened within the predefined time window or range (of around 0.1 to 0.2 seconds, for example), where the time window is defined by two values: minimum time (e.g., 0.1 second) to avoid false activation by uncontrolled squeezing, and maximum time (e.g., 0.2 second) to distinguish the squeeze action from a continuous squeeze action for changing the operating frequency when the handgrip 118 is squeezed for more that 0.2 seconds but less than 3 seconds, or activating the second type of bristles when the handgrip 118 is squeezed for more than 3 seconds, for example.

Accordingly, force and/or pressure is used to select and activate different functions. For example, three consecutive squeezes may select and activate a massage function, but two squeezes may select and activate a normal cleaning function. Further, any desired combinations of functions (e.g., massage function, a deep clean function, a light clean function, a beginner's function, a training function, a child user function, an adult user function, etc.) may also be selected and activated in response to a predefined defined frequency, pattern, amplitude, etc., even in mid-use when other functions are being performed. For example, during normal cleaning if the user were to squeeze and release three times quickly, then the massage function begins mid use until another three squeezes stops the massage and returns the toothbrush system to the normal cleaning mode or function as it was before activation of the massage function.

The selection and/or activation of the desired function(s) may also be achieved by tapping the head of the brush on the teeth, where a sensor detects the tapping of the head. Such a sensor may be similar to the described force sensors, and/or other sensors, such as at least one of a light sensor, a moisture sensor and an accelerometer. As discussed, these sensors may detect the number and/or taps intensity or force of taps of the head in the mouth, and in response, different functions are selected and/or activated. For example, two taps in the mouth may be detected by one of these sensor, and in response, the massage function may be activated. The functions may include functions such as massage function, a deep clean function, a light clean function, a beginner's function, a training function, a child user function, an adult user function, etc. Each of these functions may have a predefined defined frequency, pattern, amplitude, etc.

With force based interfaces, a user normally is able to produce and remember four to six levels of pressure/force (at least with fingers), where increasing the number of pressure levels beyond six levels could lead to the increased error rate. Further, it should be noted that since the human perception of grip force is not linear, the range of each distinguishable force level might not necessarily be of the same size. For example, the force range of what the present system might recognize as a "light grip" is smaller than the force range of what the system might recognize as a "hard grip."

To reduce false activation, a minimum activation time must first pass before activating the desired function. Thus, only if force is detected and remains within predefined range, such as 10-20 milliseconds, only then the desired function is activated. Accordingly, a delay (of 10-20 milliseconds, for example) is provided before any commencing of activation operations. Further, as typically people are not normally able to increase the pressure or the squeezing very gradually, a smoothing is performed on the detected force/pressure on the handgrip 118. Thus, if the force or squeezing continues, such as strong or stronger grip, then the reaction (i.e., operating frequency increase) is provided with some delay (before activation) and smoothing. The operating frequency may be changed gradually, or in discrete steps.

The toothbrush system 100 may be deactivated when no force or a force below a certain threshold is detected. Further, an off button or a portion of the pressure sensitive grip may be designated for deactivation function when squeezed. Alternatively or in addition, other sensor information is used to determine whether the device should be deactivated such as, for example, an accelerometer or light sensor in the grip to determine more reliably whether a user is holding the device.

In yet other embodiments, the squeezing action may be mapped to activate actuators for a desired period of time (e.g., 2 seconds, etc.) which may release a cleaning agent such as one or more of toothpaste, mouthwash, etc., or may provide a short vacuum for removing debris from teeth, etc. The various squeeze actions (e.g., squeeze actions 1, 2, and/or 3) may be selected by the user to be mapped to the squeeze action or the squeeze actions may be differentiated from each other by a type of squeeze (e.g., long, medium, or short may be mapped to a desired squeeze action such as squeeze action 1, squeeze action 2 and squeeze action 3, respectively). In some embodiments, only a single squeeze action is defined and this squeeze action may be mapped to a desired function (e.g., to activate the interdental cleaning device, etc.). In yet other embodiments, a force of the squeeze action may be mapped to speed of the toothbrush as will be described below.

In some embodiments, a state machine flow may also be used to determine a function to apply. For example, in some embodiments, after the first actuator is initially actuated (e.g., turned on) to transmit force and/or motion to the tool at a default setting (e.g., 5000 brush-strokes-per-minute (BSM)), the system may determine how much force is applied to a touch-sensitive sensor and thereafter determine a corresponding function to apply to the actuator. Thereafter, the controller may control the operation of the actuator in accordance with the determined corresponding function.

The embodiments shown above in Table 1 are just exemplary and many other settings are envisioned (e.g., for the cleaning modes, etc.). For example, in yet other embodiments, one or more of the force, patterns and corresponding cleaning mode functions may be set by the system and/or user. In yet other embodiments, a user may be identified (e.g., via a grip analysis application of the process) and a corresponding function map for the desired user may used. Thus, for example, the process may activate different functions for a first user, e.g., a parent, and a second user, e.g., a child for whom the process may activate functions for children such as a low speed (frequency) brush action, child toothpaste output, etc.

In some embodiments, the system may include an application for a user to set/reset the function selection table using a menu-based system rendered on any suitable device such as a display of the system, or display of any other connectable user device, e.g., user's phone, etc. Accordingly, the system may communicate with the user's device using any suitable communication method, such as a wired and/or wireless communication methods, e.g., Bluetooth™, etc.

In yet other embodiments, user interaction (e.g., by applied force and/or pattern) may be used to select a bristle stiffness mode in which the stiffness of the cleaning bristles may be adjusted by, for example, adjusting an extension of desired bristles (e.g., stiff bristles in the present embodiments) when a user grips the handgrip with a desired force and/or pattern. For example, when it is determined that a user squeezes the handgrip hard for more than 10 seconds, a group of stiff (hard) bristles may be extended from the brush head beyond the extension of a group of regular bristles (e.g., soft bristles) which are normally extended. Thus, embodiments of the present system may provide user interaction methods for altering the stiffness of the bristles of a brush head of the system. Although, users may prefer a toothbrush with hard bristles due to the belief that it is actually cleaning their teeth better than soft bristles, these hard bristles can, in the long term, cause damage the enamel of a user's teeth or to the gum area of a user, if overused or used excessively. Accordingly, embodiments of the present system may adjust the extension of the hard bristles so as to engage the hard bristles only when requested by user interaction. Thus, the user may interact with the OHD to alter the hardness of the bristles of a brush head when the users desires to do so such as when the user feels like the hard bristles would be desirable to, for example, remove some stubborn debris, plaque, etc.

Further, embodiments of the present system may perform a hand grip recognition method which may be used to insure that device settings are not changed when the user adjusts a handgrip on the handle during use. Thus, for example, if a user quickly changes a handgrip position, the device may ignore any changes in detected grip force and/or patterns for a certain time interval.

Figure 8A:
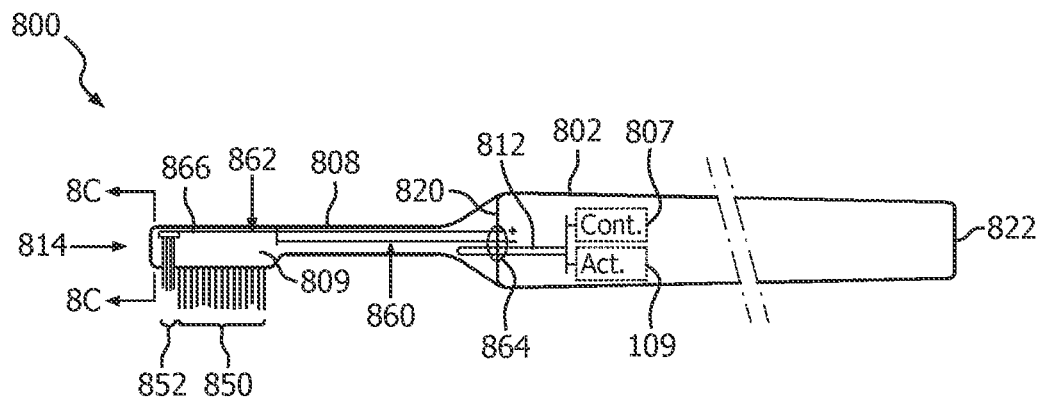
FIG. 8A shows a partially cutaway side perspective view of a portion of toothbrush system with a touch-sensitive body including an electro-active (ionic) polymer (EAP) actuator in accordance with embodiments of the present system.

FIG. 8A shows a partially cutaway side perspective view of a portion of toothbrush system 800 with a touch-sensitive (TS) body 802 in accordance with embodiments of the present system. The TS body 802 may have a first end 820 and a second end 822, a grip portion/hand grip 818 situated between the first and second ends 820, 822, and other features similar to those shown in FIG. 1, such as the touch-sensitive (TS) rings 104-1 through 104-N (generally 104-x) and/or a button-type TS sensor 106 shown in FIG. 1, but omitted from FIGS. 8A, 8B for better clarity. However, a tool 808 of the TS body 802 may include adjustable bristles as opposed to fixed bristles of the tool 108. More particularly, the tool 808 may include a brush head 814, and may be coupled to the TS body 802. The tool 808 may receive a motive force (e.g., a rotary force, a vibrational force, etc.) from any suitable force transmitting member such as an actuator rod 812. The motive force may be produced by any suitable source such as an electronic actuator (ACT) 109 coupled to the actuator rod 812, similar to that described in connection with FIG. 1, for example.

The brush head 814 may include one or more groups of bristles at least one of which is adjustable in extension. For example, a first group of bristles 850 may include bristles of a first type (e.g., soft bristles) and a second group of bristles 852 may include bristles of a second type (e.g., firm bristles). The second group of bristles 852 may be controllable so as to adjust an extension thereof relative to an exterior of the brush head 814. A bristle actuator mechanism 862 may adjust a position of the controllable bristles (e.g., the second group of bristles 852 in the present embodiment) under the control of the controller (CONT) 807 via a signal transmitted via control lines 860 so as to position the controllable bristles in a normal position (e.g., a retracted position) during normal use and in an extended position, when activation of the bristles of the second type is desired (e.g., see, Table 1 for activation methods). The bristle actuator mechanism 862 may include any suitable mechanism such as an electroactive (ionic) polymer (EAP) actuator 866 which changes its shape and/or stiffness when placed under a low voltage of, for example, 1-2 volts provided from the controller 807 via the control line 860. The EAP actuator 866 may include a passive material and, thus, can be embedded in a cavity 809 of the tool 808 with little or no additional electronics or mechanical mechanism. An electronic coupler 864 may couple the controller 807 (situated with a cavity of the TS body 802) to the EAP actuator 866 via, for example, the control line 860 so that power (e.g., a voltage such as a control voltage) may be supplied to the EAP actuator 866 as a voltage to activate the EAP actuator 866 when desired.

Figure 8B:
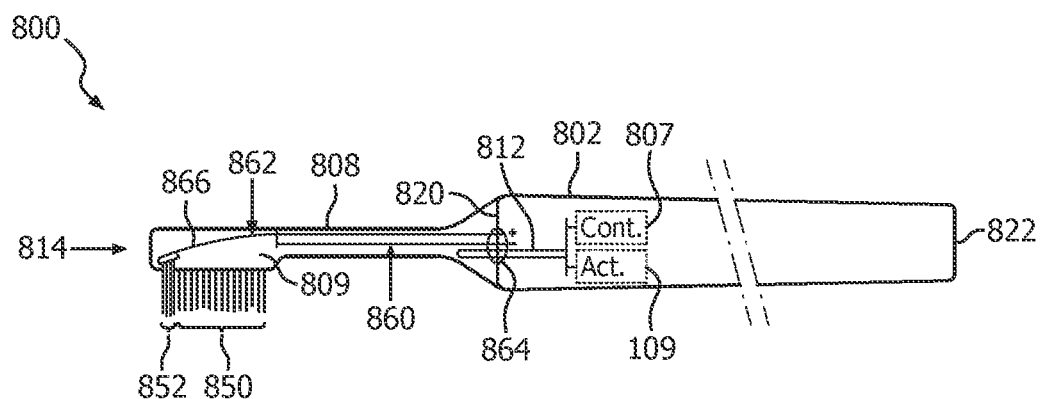
FIG. 8B shows a partially cutaway side perspective view of a portion of toothbrush system with voltage applied to the EAP actuator in accordance with embodiments of the present system.

FIG. 8B shows a partially cutaway side perspective view of a portion of toothbrush system 800 with voltage applied to the EAP actuator 866 in accordance with embodiments of the present system. As a control voltage is applied to the EAP actuator 866, the EAP actuator 866 will bend to exert a force which may cause the controllable bristles (e.g., the bristles of the second group 852) to further extend from the tool 808 so as to be able to contact a desired surface (e.g., a user's tooth) during operation. In accordance with yet other embodiments the bristles of the second group 852 may include at least one rubber wiper. In yet other embodiments, other suitable mechanisms for adjusting the position of rubber wipers and/or bristles may also be used.

Figure 8C:
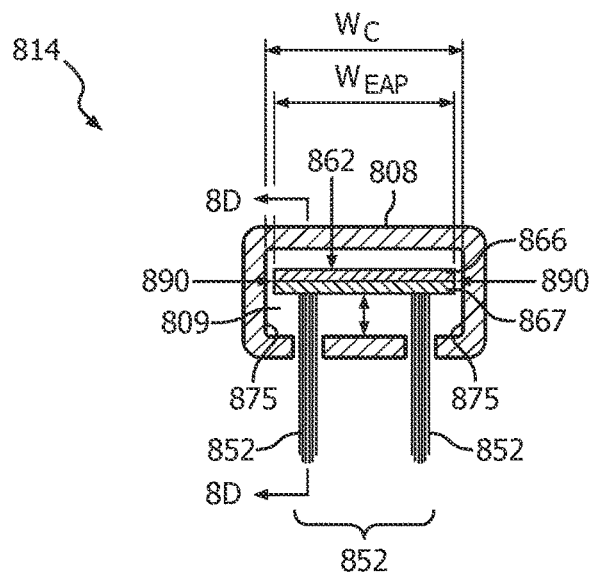
FIG. 8C shows a cross-sectional view a portion of toothbrush system taken along lines 8C-8C of FIG. 8A in accordance with embodiments of the present system.

FIG. 8C shows a cross-sectional view of a portion of toothbrush system 800 taken along lines 8C-8C of FIG. 8A in accordance with embodiments of the present system. The bristles of the second group 852 may be coupled to a carrier 867 which is, in turn, coupled to the EAP actuator 866 and situated with the cavity 809 of the tool 808. At least a portion of the cavity 809 may be defined by one or more inner edge walls 875 which may define a width ($W_c$) of the cavity 809. Similarly, the EAP actuator 866 and/or the carrier 867 may have opposed side edges 890 which may define a width ($W_{EAP}$) of the EAP actuator 866 and/or the carrier 867. The one or more inner edge walls may 875 may be configured such that Wc may be slightly greater than $W_{EAP}$ so that transverse deflection of the EAP actuator 866 and/or the carrier 867 relative to the cavity 809 of the tool 808 may be controlled (e.g., by contact of the opposed side edges 890 with adjacent ones of the one or more inner edge walls 875) when the tool 808 receives a motive force (e.g., a rotary force, a vibrational force, etc.) from any suitable force transmitting member such as the actuator rod 812 during use.

Figure 8D:
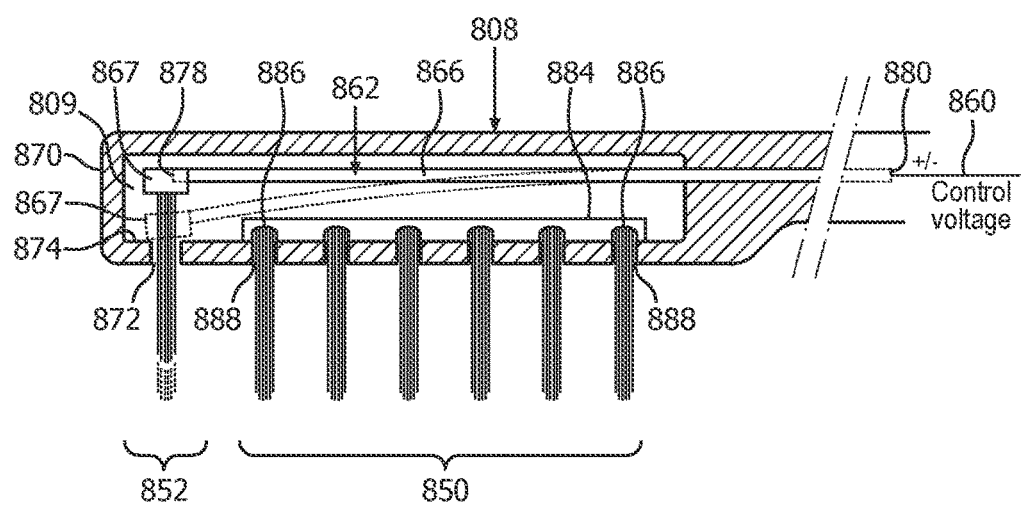
FIG. 8D shows a cross-sectional view a portion of toothbrush system taken along lines 8D-8D of FIG. 8C in accordance with embodiments of the present system.

FIG. 8D shows a cross-sectional view of a portion of the toothbrush system 800 taken along lines 8D-8D of FIG. 8C in accordance with embodiments of the present system. The tool 808 may include a body 870 having one or more side walls which may define at least part of a side of the cavity 809 and may include one or more openings 872 through which the bristles of the second group 852 may pass. For example, the cavity 809 may include an inner side wall 874 which may be configured to contact an adjacent portion of the carrier 867 when the EAP actuator 866 is bent by the control voltage as illustrated by the dotted lines. The EAP actuator 866 may have proximal and distal ends 880 and 878, respectively, and may be coupled at the proximal end 880 to the body 870 of the tool 808 so that the proximal end 880 may remain stationary relative to the body 870 when activated. Accordingly, when a control voltage is applied (e.g., when the EAP actuator is activated) to the EAP actuator 866, the EAP actuator 866 will bend and the distal 878 end of the EAP actuator 866 may be deflected to an extended position as illustrated by the dotted lines. Accordingly, the controllable bristles (e.g., the bristles of the second group 852) which are coupled to the EAP actuators 866 via the carrier 867 will be pushed through the one or more openings 872 and extend further from the tool 808 so as to be able to contact a desired surface (e.g., a user's tooth) during operation. This position may be referred to as an extended position. When the control voltage is no longer applied to the EAP actuator 866, the EAP actuator 866 resumes its normal shape as shown by the solid lines and the controllable bristles (e.g., the bristles of the second group 852) coupled thereto are retracted from their extended position so that contact with a desired surface (e.g., a user's tooth) during operation can be reduced or entirely prevented. This position may be referred to as a retracted or normal position. Thus, for example, if the bristles of the second group 852 are hard bristles, contract between these bristles and a desired surface (e.g., a user's tooth) can be reduced or entirely prevented when the bristles of the second group 852 are not extended in the retracted position. The first group of bristles 850 may be coupled to the body 870 of the tool 808 using any suitable method. For example, proximal ends 886 of the first group of bristles 850 may be coupled to first group carrier 884 which may be coupled to the body 870 of the tool 808. Accordingly, the first group of bristles 850 may pass through openings 888 which may be situated in the body 870 of the tool 808. However, in yet other embodiments, the proximal ends of the first group of bristles 850 may be coupled directly to the body 870 of the tool 808. The extension of the first group of bristles 850 may remain the fixed relative to the regardless of whether bristles of the second group 852 are extended or retracted. However, in yet other embodiments, at least some bristles of the first group of bristles 850 may be controlled to variable extend or retract similarly to the second group of bristles 852.

In accordance with embodiments of the present system, a system including an OHD having a body with a handgrip and a toothbrush coupled to the body. The handgrip may include and pressure sensor such as a force-sensitive (FS) resistor type pressure sensor. As soon as the toothbrush is switched on, a controller may determine a force applied to the pressure sensor based upon an output of the pressure sensor (e.g., an analog resistance value in the present embodiments). The force signal output by the pressure sensor may be a monotonic function of area and/or pressure applied to the pressure sensor. Further, a mapping between a force applied to the pressure sensor (e.g., as determined base upon the pressure sensor output) and a desired operation (e.g., oscillation) speed (e.g., an operating frequency) of an attached cleaning tool such as a toothbrush (e.g., in brush-strokes-per-minute (BSM)) may be provided and stored in a memory of the system.

Figure 9A:
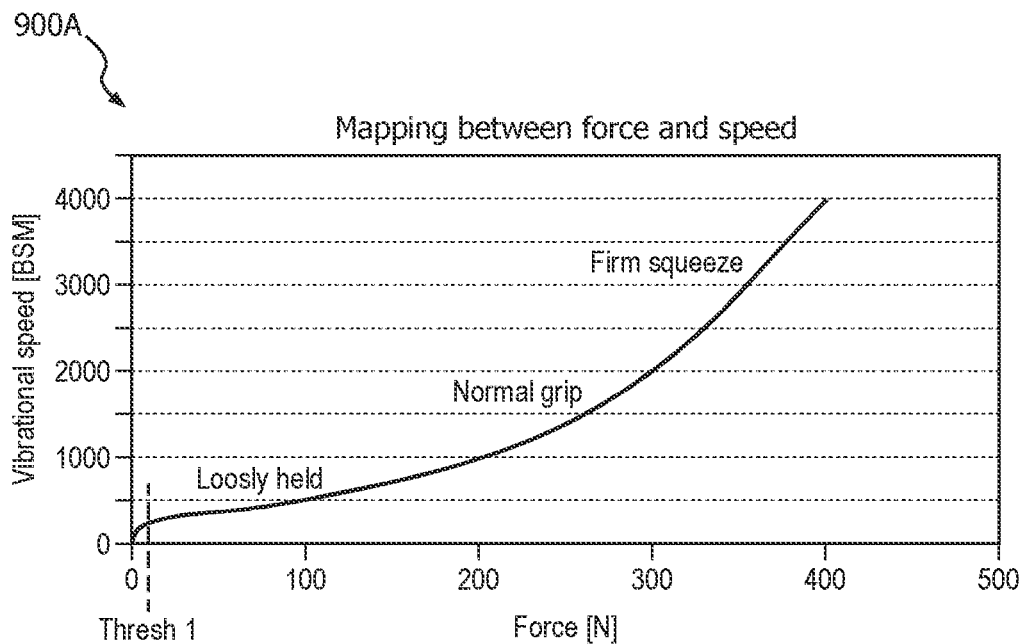
FIG. 9A shows a graph which illustrates a continuous direct relationship between the force applied to the pressure sensor(s) and brush-strokes-per-minute (BSM) values in accordance with embodiments of the present system.
Figure 9B:
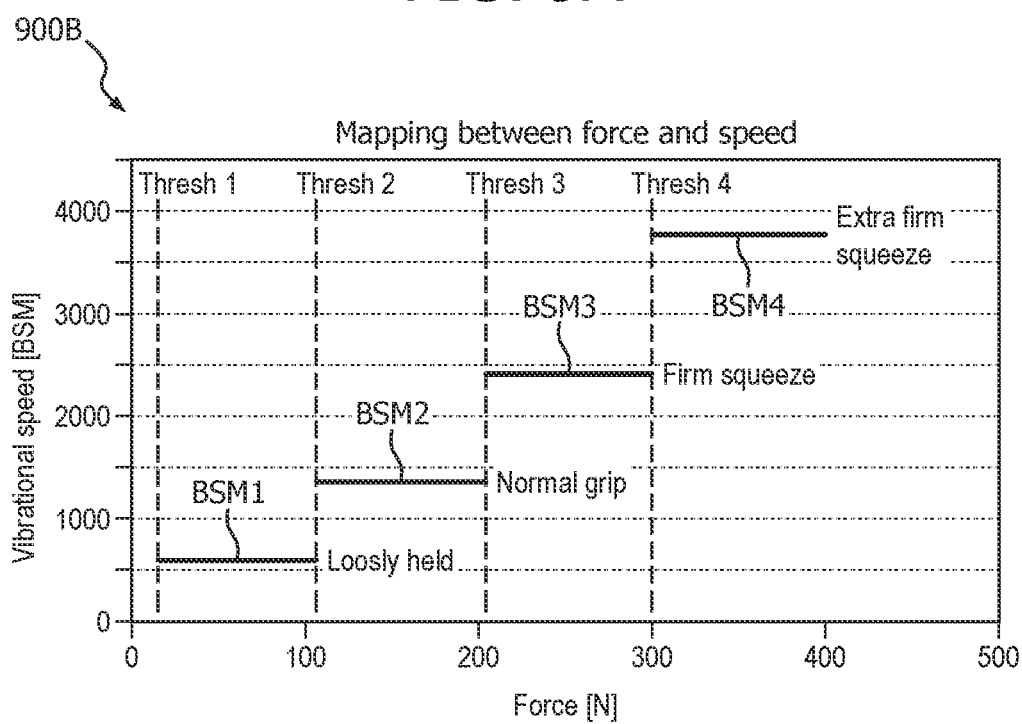
FIG. 9B shows a graph which illustrates a discrete relationship between force applied to the pressure sensor(s) and BSM values in accordance with embodiments of the present system.

The mapping may be set/reset by a user using any suitable method such as a training process performed in accordance with embodiments of the present system. For example, during the training process, a user may hold the handgrip of an OHD loosely and then gradually increase the force they apply to the on the handgrip until they exert a firm, yet comfortable, squeeze upon the handgrip. The pressure sensors on the handgrip will sense this force and form corresponding sensor information. Then, these sensor values may be converted to units of force (e.g., in Newtons (N)) which are mapped to BSM. These mapped values may then be stored in a memory of the system for later use in accordance with a user's settings. The mapped values of BSM may be related to the values output by the pressure sensors directly (e.g., continuous, on a one-to-one or linear basis) or discretely (e.g., on a discrete basis) as will be discussed below. In yet other embodiments, the signals output by the pressure sensor(s) are mapped to the BSM as discussed above without converting to units of force. For example, FIG. 9A shows a graph 900A which illustrates a direct or continuous (e.g., an on-to-one) relationship between the force applied to the pressure sensor(s) and BSM values in accordance with embodiments of the present system; and FIG. 9B shows a graph 900B which illustrates a discrete relationship between force applied to the pressure sensor(s) and BSM values in accordance with embodiments of the present system. Thus, as shown in FIG. 9A, the BSM may be mapped directly to a force applied to the pressure sensors of the handgrip on a one-to-one basis. Thus, the BSM may be directly proportional to the force applied to the handgrip. In some embodiments, the one-to-one mapping will not be applied until the sensed force exceeds a first threshold BSM, 1.

In yet other embodiments, as shown in FIG. 9B, the BSM may be mapped discretely to the FSM. Accordingly, the controller may adjust the BSM at discrete intervals in accordance with a range of pressures (e.g., "loose," "normal," and "firm") exerted by the user on handgrip as detected by the pressure sensors. For example, in some embodiments sensor information (SI) related to a force applied by a user may be obtained from a TS sensor may be compared with a plurality of threshold values (e.g., $Thresh_1$, Thresh2, Thresh3, and Thresh 4. If it is determined that: Thresh1<=SI<Thresh2, the controller may select a first BSM value (e.g., BSM1). However, if it is determined that:

Thresh2<=SI<Thresh3, the controller may select a second BSM value (e.g., BSM2). Similarly, if it is determined that: Thresh3<=SI<Thresh4, the controller may select a third BSM value (e.g., BSM3). Further, if it is determined that: Thresh4<=SI<Thresh5, the controller may select a fourth BSM value (e.g., BSM4). The mappings may be stored in a memory of the system in any suitable form such as in a function table (e.g., Table 1), if desired.

During operation of the OHD, the controller may perform operational acts such as: determining force applied to a handgrip of the OHD by a user, and determining a value for the BSM based upon the determined force. The values for the BSM may be obtained from a memory of the system (e.g., using the look-up table). Then, the controller may control the actuator in accordance with the determined value for the BSM. The actuator may then drive the brushhead at (or about) the determined value for the BSM.

In accordance with other embodiments of the present system, there is provided an OHD such as an interdental cleaning device operating in accordance with embodiments of the present system. One such interdental cleaning device is known as a such as a Philips™ AirFloss™ interdental cleaning device (IDCD) which outputs a liquid and/or gas jet when desired and may be controlled to operate in accordance with embodiments of the present system. The liquid jet may include water and/or one or more cleaning fluids such as mouthwash, a fluoride wash, an abrasive, etc.

The liquid jet may be activated in accordance with embodiments of the present system based upon a force applied to a force-sensitive (FS) pressure sensor (hereinafter pressure sensor) such as shown on the embodiments of FIGS. 1-2. Accordingly, a pressure sensor may be integrated into the hand grip of the Airfloss-type device (e.g., an IDCD) and may sense a force applied thereto by a user and provide indication of this force (e.g., as a resistive value or other sensor value) to a controller. The controller may then determine a force applied to the pressure sensor of the hand grip, a hand grip pattern, and/or a force application pattern over time. Then, the controller may determine a proper function (e.g., selected from a plurality of functions) to apply in accordance with the determined applied force, grip pattern, and/or pressure pattern over time in accordance with system and/or user settings using, for example, a table lookup. Then, the controller may activate the one or more actuators in accordance with the determined function.

Accordingly, the one or more actuators may pump a selected liquid and/or a gas in accordance with the determined function to a tool of the IDCD such as a cleaning head which may then output the liquid and/or gas from one or more openings of the cleaning head. Thus, the fluid and/or gas may be output by the cleaning head in accordance with functions based upon determined pressure, grip pattern, and/or pressure pattern over time. This may be similar to the embodiment of FIGS. 1 and 2 and the sensor output from the pressure sensors may be read by the controller. The controller may then compare a value of the sensor information from the pressure sensors to a pressure threshold value and, if it is determined that the value of the sensor information is greater than the threshold value (e.g., indicating a squeeze action of the user), the controller may control an actuator of the IDCD to supply a liquid under pressure to the cleaning head.

Alternatively, the size of the openings in the cleaning head may be altered to change the speed of the liquid and/or gas output, with a smaller opening leading to a faster output (assuming similar pressure from the pump). An actuator or motor may be provided to open and close the openings in the cleaning heads, selectively or together, such as by move a cover over the openings in the cleaning head to open and close the openings thus changing the speed of the liquid and/or gas output. Accordingly, the liquid and/or gas may be output by the cleaning head as one or more liquid/gas jets including micro-droplets of water. However, if it is determined that the value of the sensor information is less than or equal to the threshold value, no action may be taken by the controller, if desired.

Figure 10:
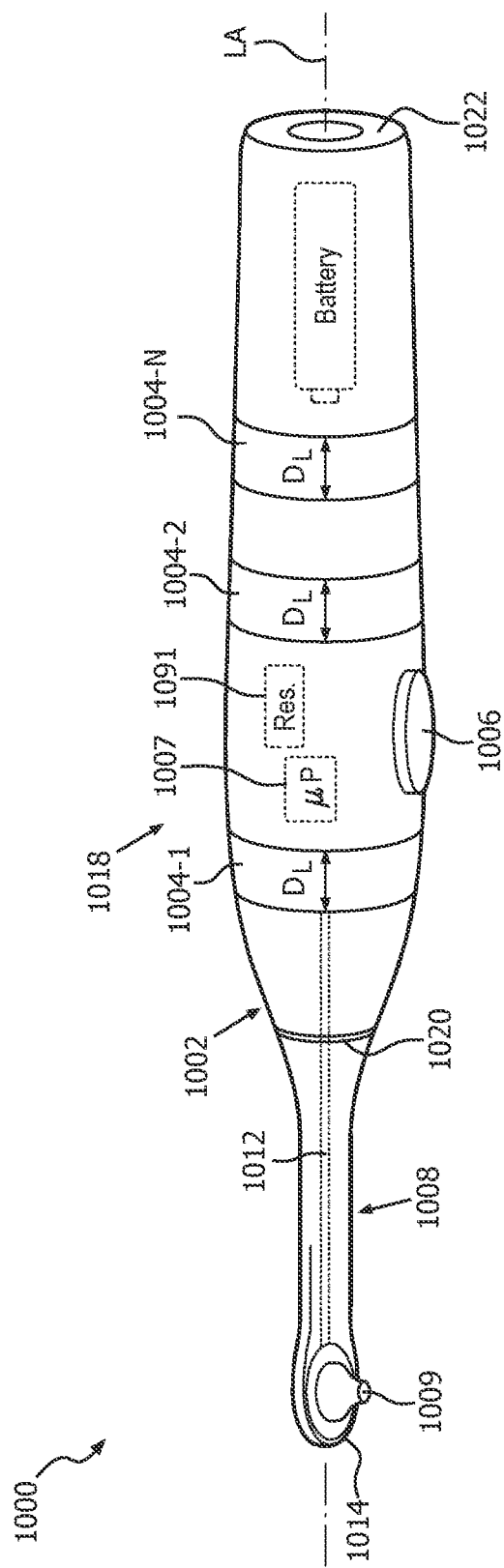
FIG. 10 shows a front perspective view of a portion of an interdental cleaning device (IDCD) system with a touch-sensitive body in accordance with embodiments of the present system.

FIG. 10 shows a front perspective view of a portion of IDCD system 1000 (hereinafter system 1000 for the sake of clarity) with a touch-sensitive body 1002 in accordance with embodiments of the present system. The IDCD system 1000 may be similar to the toothbrush system 100 shown in FIG. 1 and may include a tool 1008 for cleaning coupled to the body 1002. The touch-sensitive body 1002 may have first and second ends 1020 and 1022, respectively, a handgrip 1018 situated between the first and second ends 1020 and 1022, respectively, and one or more touch-sensitive sensors situated on the handgrip. The touch-sensitive (TS) sensors may include any suitable touch-sensitive sensing arrangement such as touch-sensitive rings 1004-1 through 1004-N (generally 1004-$x$) and/or a circular TS sensor 1006. The touch-sensitive sensors may be similar to the operation of the TS sensors 104-$x$ and 106, described in connection with FIG. 1, and may transmit information related to a force exerted thereupon to a controller of the system, such as a controller 1007, which may be a processor, such as a micro-processor µp.

With regard to the tool 1008, this tool may include a cleaning head 1014, such as an AirFloss™-type cleaning head, a liquid/water nozzle, or the like, configured to emit a liquid and/or gas as a jet (e.g., a water and/or air jet) with a given force from at least one opening 1009 of the cleaning head 1014. The opening 1009 may be flow coupled (e.g., via a conduit 1012) to one or more actuators such as one or more pumps situated in the body and which may pressurize the liquid(s) and/or gas under the control of the controller 1007. The pumps may include any suitable pump such as a rotary, reciprocal, piezo, pumps or the like. The one or more pumps may receive the liquid from any suitable source such as a hose or a reservoir (Res) 1091 flow coupled thereto. In some embodiments the cleaning head 1014 may include one or more brushes. One or more of the brushes may be extended or retracted under the control of the controller and in accordance with pressure exerted upon the handgrip 1018 as sensed by pressure sensors (1004-$x$ and/or 1006). In some embodiments, the tool may include a brush head, if desired. Further, an actuator for driving the tool may then be provided so that the tool may be driven at a desired direction(s) and/or at a desired frequency (e.g., in brush-strokes per minute (BPM)).

Figure 11:
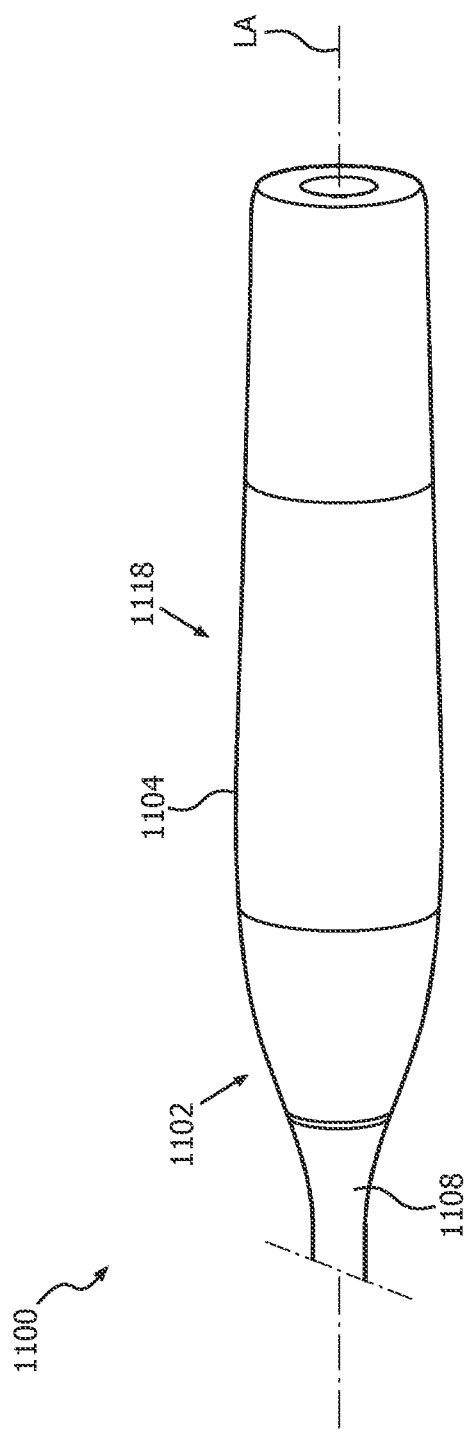
FIG. 11 shows a front perspective view of a portion of an IDCD system with a touch-sensitive body in accordance with yet other embodiments of the present system.

FIG. 11 shows a front perspective view of a portion of an IDCD system 1100 with a touch-sensitive (TS) body 1102 in accordance with yet other embodiments of the present system. The IDCD system 1100 is similar to the IDCD system 1000 and includes a body 1102, a touch-sensitive ring 1104, and a tool 1108, which are similar to the body 1002, the touch-sensitive ring 1004 (or 1004-$x$), and the tool 1008, respectively, of the IDCD system 1000. However, the touch-sensitive ring 1104 extends along a major length of a handle portion 1118 of the body 1102. Accordingly, the touch-sensitive ring 1104 may extend along a major length of the longitudinal axis (LA) of the body 1102.

Figure 12:
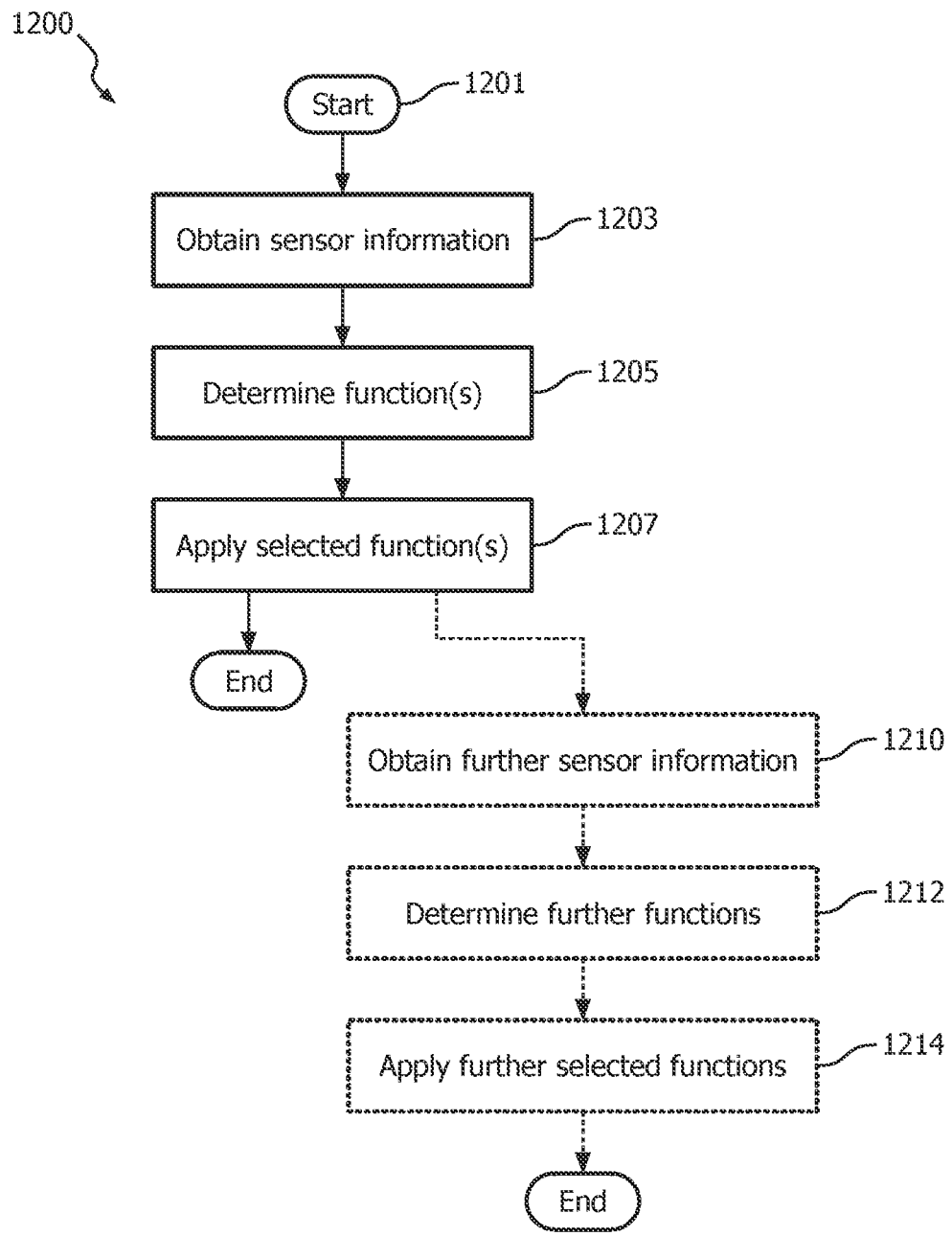
FIG. 12 which is a flow diagram that illustrates a process performed by a system in accordance with embodiments of the present system.

A method of operation of an OHD will now be discussed with reference to FIG. 12 which is a flow diagram that illustrates a process 1200 performed by a system in accordance with embodiments of the present system. The process 1200 may be performed using one or more controllers, processors or computers communicating over a network and may obtain information from, such as the controller 107 shown in FIG. 1, for example, and/or store information to one or more memories which may be local and/or remote from each other and coupled to the processor, or controller 107 for example. The process 1200 can include one of more of the following acts. Further, one or more of these acts may be combined and/or separated into sub-acts, if desired. Further, one or more of these acts may be skipped depending upon settings. In operation, the process may start during act 1201 and then proceed to act 1203.

During act 1203, the process may obtain sensor information from at least one force-sensing (FS) sensor of a handgrip portion of a body portion. The sensor information may include analog and/or digital information related to at least one value of a force applied to the at least one FS sensor by, for example, a user. For example, in some embodiments, the FS information may include information related to an area or zone at which the force is applied. In some embodiments, the FS sensor is a FS resistive sensor which may output resistance (value(s)) as the sensor information. The resistance may correspond with a force applied to the FS sensor. However, in yet other embodiments, it is envisioned that the FS sensor is a FS capacitive sensor which may output capacitance (value(s)) as the sensor information. The capacitance may correspond with a force applied to the FS sensor. After completing act 1203, the process may continue to act 1205.

During act 1205, the process, e.g., processor or controller 107, may determine and/or select a function to apply in accordance with the sensor information. Accordingly, the process may match the sensor information with function selection information stored in a memory of the system such as may be stored in a function-selection table. In some embodiments, the function selection information may include information related to one or more thresholds and/or patterns with which to compare the sensor information to and, may include corresponding functions to apply (e.g., to actuators, switches, etc.) based upon the results of the comparison(s). Once the processor determines a function to apply, corresponding actuators are controlled accordingly, e.g., to control brush stroke, a first actuator is controlled; to control fluid flow, a second actuator (e.g., a pump) is controlled; and to control brush extension, a third actuator (e.g., an EAP actuator) is controlled. After completing act 1205, the process may continue to act 1207.

During act 1207, the process, e.g., processor or controller 107, may apply the determined/selected functions. Accordingly, the processor may control or otherwise drive one or more (selected) actuators in accordance with the selected function(s). After completing act 1207, the processor may repeat act 1203 so as to continually control the OHD in accordance with input of a user or may end, if desired.

Further and/or different operational acts may be performed by the processor or controller 107 in controlling operation of the toothbrush system 800 shown in FIG. 8A, 8B having the two groups of bristles 850, 852. In particular, during act 1207, the controller 107 controls a first actuator in accordance with the selected function, where the first actuator is the same actuator (109) described in connection with FIGS. 1, 8A, 8B. In addition, during act 1210, the controller 107 obtains further sensor information generated by the touch-sensitive sensor, the further sensor information corresponding to a force applied by a user to a surface of the touch sensitive sensor at a second time. Next, during act 1212, the controller 107 determines whether the second sensor information is greater than or equal to a threshold value; and then during act 1214, the controller 107 activates a second actuator 862 to extend one of the first and second brushes 850, 852 relative to the other of the first and second brushes 850, 852 when it is determined by the determining act that the second sensor information is greater than or equal to the threshold value.

Figure 13:
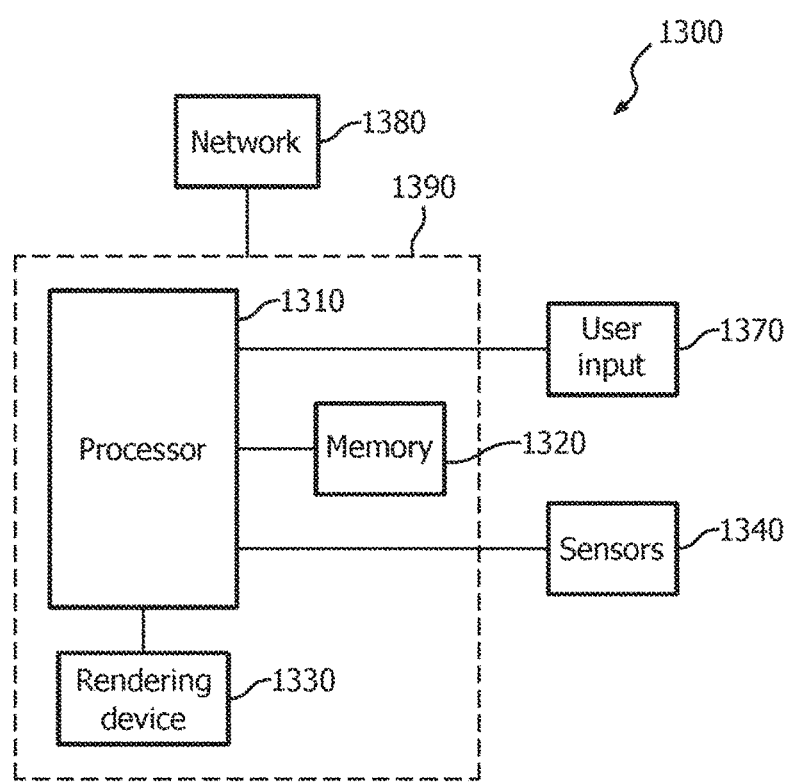
FIG. 13 shows a portion of a system in accordance with embodiments of the present system.

FIG. 13 shows a portion of a system 1300 in accordance with embodiments of the present system. For example, a portion of the present system 1300 may include a processor 1310 (e.g., a controller) operationally coupled to a memory 1320, a user interface (UI) 1330, and a user input portion 1370. The memory 1320 may be any type of device for storing application data as well as other data related to the described operation. The application data and other data are received by the processor 1310 for configuring (e.g., programming) the processor 1310 to perform operation acts in accordance with the present system. The processor 1310 so configured becomes a special purpose machine particularly suited for performing in accordance with embodiments of the present system.

The operation acts may include configuring the system 1300 by, for example, configuring the processor 1310 to obtain information from user inputs such as from the user input portion 1370 and/or the memory 1320 and processing this information in accordance with embodiments of the present system to determine function to apply and/or actuator(s) which should be controlled in accordance with a corresponding function in accordance with embodiments of the present system. The user input portion 1370 may include force-sensitive (touch-sensitive) sensors, a keyboard, a mouse, a trackball and/or other device, including touch-sensitive displays, which may be stand alone or be a part of a system, such as part of an OHD, a personal computer, a notebook computer, a netbook, a tablet, a smart phone, a personal digital assistant (PDA), a mobile phone, and/or other device for communicating with the processor 1310 via any operable link. The user input portion 1370 may be operable for interacting with the processor 1310 including enabling interaction within a UI as described herein. Clearly the processor 1310, the memory 1320, the UI 1330 and/or user input portion 1370 may all or partly be a portion of a computer system or other device such as a client and/or server as described herein.

The processor 1310 may render the information on the UI 1330 such as on a display of the system (e.g., graphics capable display, light emitting diodes (LEDs), a liquid crystal display (LCD), etc.

The methods of the present system are particularly suited to be carried out by processor programmed by a computer software program, such program containing modules corresponding to one or more of the individual steps or acts described and/or envisioned by the present system.

The processor 1310 is operable for providing control signals and/or performing operations in response to input signals from the user input portion 1370 as well as in response to other devices of a network and executing instructions stored in the memory 1320. For example, the processors 1310 may obtain feedback information from the feedback sensors and may process this information to determine force applied to a cleaning tool, if desired. The processor 1310 may include one or more of a microprocessor, an application-specific or general-use integrated circuit(s), a logic device, etc. Further, the processor 1310 may be a dedicated processor for performing in accordance with the present system or may be a general-purpose processor wherein only one of many functions operates for performing in accordance with the present system. The processor 1310 may operate utilizing a program portion, multiple program segments, or may be a hardware device utilizing a dedicated or multi-purpose integrated circuit.

Accordingly, for an optimal cleaning experience, embodiments of the present system may enable users to control various functions of an oral healthcare device such an electronic toothbrush and/or flosser. For example, embodiments of the present system may provide for a user to control the speed of an electronic toothbrush and/or a jet of water ejected from an automatic flosser (e.g., an Airfloss™-type device). What is optimal for a user may depend on various factors such as: a desired efficacy, personal preferences, amount of dirt, type of dirt, sensitivity, pain threshold, spacing between the teeth, etc. Accordingly, a user may map functions to hand grip force, patterns, etc.

Accordingly embodiments of the present system provide systems, apparatus, and methods which may allow users to easily control operating parameters of an oral healthcare device. For example, rather than having to press buttons on a console of the toothbrush to select the operational mode, the user may easily exercise control to select various functions of an electronic toothbrush or flosser operating in accordance with embodiments of the present system by, for example, adjusting pressure (e.g., by squeezing harder or softer on the handgrip) on a pressure-sensitive handgrip of the electronic toothbrush or flosser. The pressure-sensitive hand grip may be squeezed during use to select functions such as a shot of air or application of stiffer bristles to remove some stubborn debris etc. which may be desirable at different times during a cleaning operation. By providing a touch-sensitive hand grip, a user does not have to make visual contact with the console of the toothbrush or flosser to see where to press to select a function. Further, a handgrip of the electronic toothbrush or flosser may have a smooth surface without physical buttons, which makes the electronic toothbrush or flosser easier to clean and more hygienic.

While the present invention has been shown and described with reference to particular exemplary embodiments, it will be understood by those skilled in the art that present invention is not limited thereto, but that various changes in form and details, including the combination of various features and embodiments, may be made therein without departing from the spirit and scope of the invention. For example, instead of a toothbrush or an oral cleaning device, the present system is equally applicable to items used by dentists such as drills and/or optical camera or viewing apparatus for diagnostics etc. Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, the section headings included herein are intended to facilitate a review but are not intended to limit the scope of the present system. Accordingly, the specification and drawings are to be regarded in an illustrative manner and are not intended to limit the scope of the appended claims.

The section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated; and i) the term "plurality of" an element includes two or more of the claimed element, and does not imply any particular range of number of elements; that is, a plurality of elements may be as few as two elements, and may include an immeasurable number of elements.

The invention claimed is:

1. An oral cavity apparatus, comprising:
   a body portion having first and second ends and a grip portion;
   an oral tool coupled to the first end of the body portion;
   a touch-sensitive (TS) sensor that includes a plurality of pressure zones which is located on the body portion and outputs a sensor value indicative of pressure zones to which a force is applied thereto by a user; and
   a controller configured to identify the user in response to recognizing a pressure pattern in the sensor value via a grip analysis, the controller further being configured to use a corresponding function map of different cleaning functions for (i) a first identified user and (ii) a second identified user when subsequently comparing the sensor value with at least one threshold value, and to actuate the oral tool based upon the results of (i) the comparison and (ii) the corresponding function map for the first or second identified user.

2. The oral cavity apparatus of claim 1, wherein the oral tool comprises at least one of a toothbrush, a water-based inter-dental cleaning device, and a drill.

3. The oral cavity apparatus of claim 2, wherein the TS sensor comprises a force-sensitive resistor which outputs a value of resistance.

4. The oral cavity apparatus of claim 3, wherein the TS sensor comprises a plurality of polymer layers which are laminated upon each other and which substantially encircle the body portion.

5. The oral cavity apparatus of claim 1, wherein the controller is further configured to determine a frequency to reciprocally drive the oral tool in accordance with results of the comparison.

6. The oral cavity apparatus of claim 1, wherein to actuate the oral tool, the controller controls an actuator which is coupled to the oral tool to provide an electromotive force to the oral tool.

7. The oral cavity apparatus of claim 1, wherein the sensor value is a resistive value which is proportional to the force applied to the TS sensor.

8. The oral cavity apparatus of claim 1, further comprising an actuator coupled to the oral tool, wherein the actuator comprises at least one of a rotary motor, a linear motor, and a pump.

9. The oral cavity apparatus of claim 8, wherein the actuator comprises the pump, the apparatus further comprising a fluid reservoir coupled to the pump.

10. The oral cavity apparatus of claim 1, wherein the controller is further configured to determine a frequency to drive the oral tool in accordance with the sensor value based upon one of a one-to-one basis and a discrete basis.

11. A method of actuating an oral cavity apparatus having a body portion and an oral tool extending from the body portion, the oral tool coupled to an actuator, the body portion having a grip portion situated between opposed ends of the body portion, the method performed by at least one controller of the oral cavity apparatus and comprising steps of:
    obtaining sensor information generated by a touch-sensitive (TS) sensor that includes a plurality of pressure zones situated at the grip portion of the body portion, the sensor information corresponding to pressure zones to which a force is applied thereto by a user to a surface of the TS sensor;
    selecting a cleaning function from a plurality of functions based upon the sensor information, wherein selecting comprises first identifying the user in response to recognizing a pressure pattern in the sensor information via a grip analysis, and then using a corresponding function map of different cleaning functions for (i) a first identified user and (ii) a second identified user when subsequently comparing the sensor information with at least one threshold value; and
    controlling the actuator in accordance with the selected cleaning function based upon results of (i) the comparison and (ii) the corresponding function map of the first or second identified user.

12. The method of claim 11, further comprising a step of forming, by the TS sensor, the sensor information to comprise an impedance value corresponding to the force applied by the user to the surface of the TS sensor.

13. The method of claim 11, wherein the step of selecting a second from a plurality of functions comprises a step of determining a frequency at which to drive the actuator in accordance with the sensor information on one of a one-to-one and a discrete basis.

14. The method of claim 11, further comprising a step of controlling a second actuator to control an extension of bristles from the oral tool in accordance with the selected function.

15. A non-transitory computer readable medium comprising computer instructions which, when executed by a processor, configure the processor to control operation of an oral cavity apparatus having a body portion and an oral tool extending from the body portion, the oral tool coupled to an actuator, the body portion having a grip portion situated between opposed ends of the body portion, wherein the processor controls the operation by performing acts of:
    obtaining sensor information generated by a touch-sensitive (TS) sensor that includes a plurality of pressure zones situated at the grip portion of the body portion, the sensor information corresponding to pressure zones to which a force is applied thereto by a user to a surface of the TS sensor;
    selecting a cleaning function from a plurality of functions based upon the sensor information, wherein selecting comprises first identifying the user in response to recognizing a pressure pattern in the sensor information via a grip analysis, and then using a corresponding function map of different cleaning functions for (i) a first identified user and (ii) a second identified user when subsequently comparing the sensor information with at least one threshold value; and
    controlling the actuator in accordance with the selected cleaning function based upon results of (i) the comparison and (ii) the corresponding function map of the first or second identified user.

* * * * *